US012102705B2

(12) United States Patent
Mancini et al.

(10) Patent No.: US 12,102,705 B2
(45) Date of Patent: Oct. 1, 2024

(54) PEPTIDES HAVING INHIBITORY ACTIVITY ON MUSCARINIC RECEPTOR M3

(71) Applicant: AZIENDE CHIMICHE RIUNITE ANGELINI FRANCESCO—A.C.R.A.F. S.p.A., Rome (IT)

(72) Inventors: Francesca Mancini, Nettuno (IT); Isabel Devesa Giner, Elche (ES); Antonio Ferrer Montiel, Alicante (ES); Gregorio Fernandez Ballester, Murcia (ES); Giorgina Mangano, Rome (IT); Cristina Bartella, Rome (IT)

(73) Assignee: AZIENDE CHIMICHE RIUNITE ANGELINI FRANCESCO—A.C.R.A.F. S.p.A., Rome (IT)

( * ) Notice: Subject to any disclaimer, the term of this patent is extended or adjusted under 35 U.S.C. 154(b) by 764 days.

(21) Appl. No.: 15/734,033

(22) PCT Filed: Jun. 11, 2019

(86) PCT No.: PCT/EP2019/065223
§ 371 (c)(1),
(2) Date: Dec. 1, 2020

(87) PCT Pub. No.: WO2019/238686
PCT Pub. Date: Dec. 19, 2019

(65) Prior Publication Data
US 2022/0142898 A1 May 12, 2022

(30) Foreign Application Priority Data
Jun. 13, 2018 (EP) .................................... 18177587

(51) Int. Cl.
| | |
|---|---|
| A61K 8/64 | (2006.01) |
| A61K 38/00 | (2006.01) |
| A61Q 15/00 | (2006.01) |
| C07K 5/117 | (2006.01) |
| C07K 7/06 | (2006.01) |
| C07K 7/08 | (2006.01) |

(52) U.S. Cl.
CPC ................ *A61K 8/64* (2013.01); *A61Q 15/00* (2013.01); *C07K 5/1024* (2013.01); *C07K 7/06* (2013.01); *C07K 7/08* (2013.01); *A61K 38/00* (2013.01)

(58) Field of Classification Search
CPC .......... A61K 8/64; A61K 38/00; A61Q 15/00; C07K 5/1024; C07K 7/06; C07K 7/08
See application file for complete search history.

(56) References Cited

U.S. PATENT DOCUMENTS

| | | |
|---|---|---|
| 7,479,281 B1 | 1/2009 | Walker |
| 2002/0086036 A1 | 7/2002 | Walker |
| 2003/0133912 A1 | 7/2003 | Davidson et al. |
| 2004/0072238 A1 | 4/2004 | Yamano et al. |
| 2005/0282755 A1 | 12/2005 | Hart et al. |
| 2006/0216739 A1 | 9/2006 | Yamano et al. |
| 2006/0292554 A1 | 12/2006 | Held et al. |
| 2008/0241960 A1 | 10/2008 | Yamano et al. |
| 2010/0272754 A1 | 10/2010 | Walker |
| 2011/0097743 A1 | 4/2011 | Bihain et al. |
| 2011/0104723 A1 | 5/2011 | Pemberton et al. |
| 2012/0114703 A1 | 5/2012 | Walker |
| 2013/0247236 A1 | 9/2013 | McWhirter et al. |
| 2015/0098989 A1* | 4/2015 | Ferrer Montiel ....... A61P 25/00 424/59 |
| 2015/0140017 A1 | 5/2015 | Dhodapkar et al. |
| 2015/0183827 A1 | 7/2015 | Milletti |
| 2016/0132631 A1 | 5/2016 | Bremel et al. |
| 2018/0051050 A1 | 2/2018 | Pemberton et al. |
| 2018/0094030 A1 | 4/2018 | Milletti |
| 2018/0141998 A1 | 5/2018 | Nguyen et al. |

FOREIGN PATENT DOCUMENTS

| | | | | |
|---|---|---|---|---|
| EP | 1 295 939 A1 | 3/2003 | | |
| EP | 2071334 A1 * | 6/2009 | ............. | C07K 16/32 |
| JP | WO 2013/125221 A1 | 8/2013 | | |
| WO | WO 98/45322 A2 | 10/1998 | | |
| WO | WO 03/050238 A2 | 6/2003 | | |
| WO | WO 2005/090385 A2 | 9/2005 | | |
| WO | WO 2005/118647 A2 | 12/2005 | | |
| WO | WO 2005/118647 A3 | 12/2005 | | |
| WO | WO 2007/048022 A2 | 4/2007 | | |
| WO | WO 2009/100348 A2 | 8/2009 | | |
| WO | WO 2009/100348 A3 | 8/2009 | | |
| WO | WO 2009/113879 A1 | 9/2009 | | |
| WO | WO 2013/040142 A2 | 3/2013 | | |
| WO | WO 2013/153191 A1 | 10/2013 | | |
| WO | WO 2013/172926 A1 | 11/2013 | | |
| WO | WO 2014/001229 A2 | 1/2014 | | |
| WO | WO 2014/200910 A2 | 12/2014 | | |
| WO | WO 2016/172722 A1 | 10/2016 | | |
| WO | WO 2017/120222 A1 | 7/2017 | | |
| WO | WO 2018/223092 A1 | 12/2018 | | |

OTHER PUBLICATIONS

Smith et al., "Nucleic acids to amino acids: DNA Specifies Protein" in Nature Education 1(1):126, 2008. (Year: 2008).*

(Continued)

*Primary Examiner* — Blessing M Fubara
(74) *Attorney, Agent, or Firm* — Oblon, McClelland, Maier & Neustadt, L.L.P.

(57) ABSTRACT

Peptides able to inhibit the muscarinic receptor M3 activity and to products comprising such peptides, in particular pharmaceutical and cosmetic products useful for ameliorating skin conditions mediated by the muscarinic receptor M3 activity, such as excessive perspiration, inflammation, sebum production, and cell adhesion, motility, growth, differentiation and proliferation.

18 Claims, No Drawings

Specification includes a Sequence Listing.

(56) References Cited

OTHER PUBLICATIONS

Office Action issued Jan. 25, 2024, in corresponding European Patent Application No. 19 729 034.9, 10 pages.
Sakina Kiyoshi et al.: "Thermolysin-catalyzed synthesis of peptide amides.", Chemical and Pharmaceutical Bulletin, vol. 36, No. 11, Jan. 1, 1988, pp. 4345-4354, XP093121466.
Huybrechts J. et al.: "Neuropeptide and neurohormone precursors in the pea aphid, *Acyrthosiphon pisum*", Insect Molecular Biology, vol. 19, Mar. 1, 2010, pp. 87-95, XP093025481.
"Search Directed to Analogs of SEQ ID No. 5", XP093121573, 255 pages.
International Search Report and Written Opinion issued on Oct. 17, 2019 in PCT/EP2019/065223 filed on Jun. 11, 2019.
Gilliam, A. J. H. et al., "Affinity-Guided Design of Caveolin-1 Ligands for Deoligomerization," Journal of Medicinal Chemistry, vol. 59, No. 8, 2016, pp. 4019-4025, XP55492359.
Protas, A. M. et al., "Sequence-specific Ni(II)-dependent peptide bond hydrolysis for protein engineering: Active sequence optimization," Journal of Inorganic Biochemistry, vol. 127, 2013, pp. 99-106, XP028712770.
Toma, A. et al., "Recognition of Human Proinsulin Leader Sequence by Class I-Restricted T-Cells in HLA-A*0201 Transgenic Mice and in Human Type 1 Diabetes," Diabetes, vol. 58, No. 2, 2009, pp. 394-402, XP002677791.
Smith, B. D. et al., "Genetic selection for peptide inhibitors of angiogenin," Protein Engineering, Design & Selection, vol. 21, No. 5, 2008, pp. 289-294, XP55604942.

\* cited by examiner

SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Trp Met Arg Leu
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Trp Met Arg Leu Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 3

Trp Met Arg Leu Lys Ala
1               5

<210> SEQ ID NO 4

```
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Trp Met Asn Leu Lys Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Trp Met Phe Leu Lys
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Arg Met Tyr Lys Met Met Ala Gly Met Tyr Leu Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 7

Arg Val Met Tyr Lys Met Asn Lys Arg Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Arg Val Met Phe Lys Met Phe Lys Arg Asp Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 9

Arg Met Thr Met Leu Met Leu Asp Phe Lys Tyr Met Lys Trp Trp
1               5                   10                  15

<210> SEQ ID NO 10
<211> LENGTH: 15
```

```
<212> TYPE: PRT
<213> ORGANISM: Artificial Sequence
<220> FEATURE:
<223> OTHER INFORMATION: Synthetic Peptide

<400> SEQUENCE: 10

Lys Met Thr Met Arg Met Leu Tyr Phe Lys Tyr Met Met Trp Trp
1               5                   10                  15
```

PEPTIDES HAVING INHIBITORY ACTIVITY ON MUSCARINIC RECEPTOR M3

SEQUENCE LISTING

The instant application contains a Sequence Listing which has been submitted electronically in ASCII format and is hereby incorporated by reference in its entirety. Said ASCII copy, created on May 10, 2021, is named 533695USSL.txt and is 2,298 bytes in size.

FIELD OF THE INVENTION

The present invention relates to peptides able to inhibit the muscarinic receptor M3 activity and to products comprising such peptides, in particular pharmaceutical and cosmetic products useful for ameliorating skin conditions mediated by the muscarinic receptor M3 activity, such as excessive perspiration, inflammation, sebum production, and cell adhesion, motility, growth, differentiation and proliferation.

STATE OF THE ART

Acetylcholine (ACh) is a classical well-known neurotransmitter involved in the cholinergic transmission at both central (CNS) and peripheral (PNS) nervous system. At CNS level, cholinergic receptors are recognized as binding and effector proteins for ACh mediating chemical neurotransmission at neurons, ganglia, interneurons and the motor endplate. As for PNS, neurotransmitter ACh acts through its receptors regulating heart rate, smooth muscle contraction and stimulating glandular secretion (Wessler et al., Br. J. Pharmacol. 2008, 154, 1558-1571; Wessler et al., Handb. Exp. Pharmacol. 2012, (208):469-491). Lately, the concept of non-neuronal cholinergic system (NNCS) has emerged, conferring to ACh a hormonal function with auto- and paracrine mechanism of action. These systems appear in a wide variety of cells types and non-neuronal tissues, most of them not directly innervated by cholinergic neurons (Kurzen et al., Horm. Metab. Res. 2007, 39, 125-135). These tissues express all receptor subtypes and signal-transduction pathways including ACh-synthesizing enzymes, transporters, receptors and degrading enzymes required for Ach system (Beckman et al., Pharmacology, 2013, 92, 286-302). Acetylcholine is the main neurotransmitter responsible of sweating through binding to the cholinergic receptors on the eccrine gland. Nevertheless, acetylcholine is a prototypical neurotransmitter that has recently been recognized to occur also extra-neuronally in a large variety of cells (Kurzen et al., Horm. Metab. Res., 2007, 39(2), 125-135). Emerging evidences suggest that the cholinergic system in non-neuronal tissues, such as the placenta, is differently regulated from that in neuronal tissues. For instance, ACh molecule is released differentially between neuronal and non-neuronal cells, proposing Organic Cation Transporters as the main players in ACh release in contrast to neuronal vesicle exocytosis. Furthermore, cholinergic receptors expression pattern in the non-neuronal system varies within the same cell type depending on state of cell differentiation and activity, as well as with cell environmental conditions. Therefore, understanding the cholinergic system and its regulation of non-neuronal context will lead to unveil new aspects on acetylcholine circuit regulation under physiological and pathophysiological conditions.

Skin is one of the best-known NNCS organs, where cholinergic system is implicated in numerous functions such as growth and differentiation, adhesion and motility, barrier formation, sweat and sebum secretion (Nana et al., Life Sci. 2007, 80(24-25), 2214-2220). ACh is produced in keratinocytes, endothelial cells and most notably in immune competent cells invading the skin at sites of inflammation. For instance, in atopic dermatitis, ACh levels are elevated 14-fold in the superficial epidermis and upper dermis and 3-fold in the underlying dermis and hypodermis with an important involvement of non-neuronal ACh. Therefore, revealing the role of the non-neuronal cholinergic system in this skin condition will help to develop new strategies to treat atopic dermatitis (Wessler et al., Life Sci. 2003; 72 (18-19), 2169-2172; Beckman et al., Pharmacology, 2013, 92, 286-302).

The NNCS on skin plays and intermediary role in cell interaction with the external environment, hormones, growth factors, cytokines and the neural system. In this regard, expression of cholinergic receptors is part of the auto- and paracrine regulatory loop of non-neuronal ACh released from these cells. As for nervous system, ACh acts on skin cells trough nicotinic and muscarinic receptors, that are widely expressed in the integumentary system. In particular, nicotinic receptors seem to be expressed with high variability in the epidermis, varying along with skin cell types, differentiation process and putative influencing factors including age, atopic disposition and external factors (Nana et al., Life Sci. 2007; 80(24-25), 2214-2220). In contrast, muscarinic receptors expression pattern seems to be well-defined on this particular tissue. Muscarinic receptors are a group of 5 members G-protein-coupled receptors subdivided into two subgroups: M2 and M4 receptors are inhibitory receptors coupled to $G_{i/o}$ affecting the adenylyl cyclase activity and inhibiting non-selective cation channels, transient receptor potential channels and potassium channels. M1, M3 and M5 receptors are coupled to $G_{q/11}$ and considered as excitatory receptors since they increase intracellular calcium via generation of inositol 1,4,5-triphosphate and 1,2-diacylglycerol. All five subtypes of muscarinic receptors appear on all skin cell types i.e. keratinocytes, pilosebaceous unit, sweat glands, melanocytes and fibroblasts. In particular, keratinocytes of human epidermis expresses muscarinic receptors (Kurzen et al., Horm. Metab. Res. 2007, 39, 125-135) in which M1 and M4 are present in the upper spinous and granular layers and M2, M3 and M5 receptors appear in basal layers. In many autocrine functions of ACh, Gq-coupled muscarinic receptors have been implicated, with the majority of data relating to M1, M3 and M4. In particular, M1 receptor activation in terminally differentiated keratinocytes elicits secretion of a humectant substance on skin surface in response to locally released acetylcholine pointing to M1 receptor being an important candidate on skin homeostasis regulation (Nguyen et al., J. Cell. Sci. (2001) 114, 1189-1204).

On the other hand, M3 and M4 are relevant players on maintenance of epidermal barrier. M3 receptor stimulation up-regulates the binding activity of β1-integrin, which is associated with increased cell adhesion to extracellular matrix proteins (Quigley et al., Chest. 1998, 114(3):839-846; Williams et al., Life Sci. (2003), 72, 2173-2182; Varker et al., Biochem Pharmacol. 2002, 63(4): 597-605). Likewise, M3 receptor inhibition by antisense oligonucleotides resulted in cell detachment and changes in the expression levels of E-cadherin and β- and γ-catenins promoting cell detachment and migration. Reciprocally, M4 activation stimulates migration and induces expression of migratory integrins while inhibition evoked up-regulation of sedentary integrins (Chernyaysky et al., J. Cell. Biol. 2004, 166(2):

261-272). Thus, M3 and M4 receptors exhibited reciprocal effects on lateral migration in keratinocytes. These results indicated that selective muscarinic receptors regulation may serve to modulate abnormal keratinocytes migration, such as wound healing disorders (Uberti et al., Cells Tissues Organs, 2017, 203: 215-230).

Designing novel compounds targeting muscarinic receptors for skin conditions opens a wide scope of applications since both neuronal and non-neuronal receptors would be involved. From ACh neuronal context release, M3 activation is considered the main responsible in sweat generation and secretion produced by eccrine glands. The eccrine glands are the major responsible for physiological sweating, triggered by either psychological or thermal stimuli. Present over the whole body surface, M3 shows higher expression level on the palms and soles, which is equivalent to emotional sweating affected areas. Mainly innervated by cholinergic fibres, acetylcholine M3 activation on eccrine gland activation induces sweat production.

Muscarinic receptors have been used as target for hyperhidrosis treatments. In fact, local administration of muscarinic antagonist atropine attenuates or abolishes sweating (Shibasaki et al., Front Biosci. 2010, 2: 685-696; 2010; Kolka et al., Aviat Space Environ Med. 1987, 58(6): 545-549; Foster et al., J Physiol. 1970, 210(4): 883-895). For instance, topical application of off-label anticholinergic glycopyrrolate is an effective treatment for focal hyperhidrosis (Baker D M, J Eur Acad Dermatol Venereol. 2016, 30(12), 2131-2136; Pariser et al., Dermatol Clin. 2014, 32(4), 485-490). Furthermore, oral administration of anti-muscarinic therapies is also currently used to treat hyperhidrosis (Gordon et al., Dermatol. Ther. 2013, 26(6): 452-461). However, despite the collection of existing compounds, most of the treatments on the market cause undesirable side effects in patients, such as irritation and urinary retention (Baker D M, J. Eur. Acad. Dermatol. Venereol. 2016, 30(12), 2131-2136; Pariser et al., Dermatol. Clin. 2014, 32(4):485-490) mainly due to the poor selectivity of molecules among muscarinic receptors. Thus, development of alternatives to the already existing compounds in the prior art of the hyperhidrosis treatment is still in the focus of cosmetic and pharmaceutical sector to obtain innovative active ingredients to improve efficacy and reduce side effects on hyperhidrosis treatment or with potential antiperspirant properties for skin care conditions.

Overall, novel selective compounds specifically targeting muscarinic receptors subtypes are required to develop effective treatments on skin conditions. One of the main difficulties on selective compound design is the strong sequence similarity among all five muscarinic subtypes. Specifically, amino acids from the orthosteric binding site are perfectly conserved in all five subtypes, hindering to obtain effective subtype-selective ligands. Therefore, new regions of the receptors should be considered to design novel muscarinic modulators, such as sequences involved in allosteric modulation, subunits oligomerization or protein-protein interaction. In this regard, high-resolution X-ray structure of the M3 receptor is promising tool to identify compounds selectively binding on specific regions on the receptor.

In conclusion, this invention provides an alternative to the existing need and comprises the discovery of novel peptide sequences capable of inhibiting M3 activation and products including such peptides, in particular cosmetic products having predictable non-therapeutic skin care application implying cell adhesion, motility, growth, differentiation, barrier formation, sebum secretion, inflammation, such as, for example, wound healing, acne, and dermatitis.

SUMMARY OF THE INVENTION

The Applicant has surprisingly found peptides able to inhibit, or at least reduce, the acetylcholine-induced activity of muscarinic receptor M3 subtype by interacting with M3 intracellular regions. This mechanism affects structural rearrangements within the protein and/or protein-protein interactions necessary to activate the receptor. These compounds are useful for the treatment and/or care of skin conditions, disorders and/or diseases, which are improved or prevented by M3 receptor inhibition, such as, for example wound healing disorders, excessive perspiration and hyperhidrosis.

The Applicant has found that the peptides having the following sequences nos. 1 to 10 have an inhibitory effect on acetylcholine-M3 activation. Even if the exact molecular mechanism has not yet fully elucidated and confirmed, and without being bound by any theory, the inventors believe that the inhibitory effect on acetylcholine-M3 activation is due to the capability of the peptides to act against cytosolic regions of M3, in particular by acting as antagonist competitor for the M3-Gq-alpha protein complex, so impairing downstream cascade signalling.

Specifically, the sequences nos. 1 to 10 of the peptides which inhibit M3 activity of the invention are detailed hereinbelow:

```
                                          Seq. ID No. 1
         WMRL

Seq. ID No. 2
         WMRLK

Seq. ID No. 3
         WMRLKA

Seq. ID No. 4
         WMNLKT

Seq. ID No. 5
         WMFLK

Seq. ID No. 6
         RMYKMMAGMYLR

Seq. ID No. 7
         RVMYKMNKRDY

Seq. ID No. 8
         RVMFKMFKRDY

Seq. ID No. 9
         RMTMLMLDFKYMKWW

Seq. ID No. 10
         KMTMRMLYFKYMMWW
```

The Applicant has also found that the M3 inhibition is also obtained with sequences having a length of not more than 20 amino acids and comprising the above described sequences nos. 1 to 10, or a sequence having at least 70%, preferably at least 80%, and more preferably at least 90% sequence identity with any one of the sequences nos. 1 to 10.

The Applicant has also found that M3 inhibition can be modulated by linking to the N-terminus of the above described sequences nos. 1 to 10 an alkyl carbonyl group, such as, for example, an acetyl group, a palmitoyl group, or a myristoyl group as well as by forming a salt of the above described sequences nos. 1 to 10 with a suitable anion, such as, for example, chloride, acetate or trifluoroacetate.

Accordingly, a first aspect of the present invention relates to peptides having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences nos. ID 1 to 10, and a derivative or salt thereof.

A second aspect of the present invention relates to a pharmaceutical or cosmetic composition comprising (i) a peptide having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences ID nos. 1 to 10, and a derivative or salt thereof, and (ii) at least one pharmaceutically or cosmetically acceptable ingredient.

A third aspect of the present invention relate to the use of a peptide having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences ID nos. 1 to 10, and a derivative or salt thereof for ameliorating skin conditions mediated by the muscarinic receptor M3 activity.

A fourth aspect of the present invention relates to a therapeutic or non-therapeutic method for ameliorating skin conditions mediated by the muscarinic receptor M3 activity comprising the topical application of a pharmaceutical or cosmetic composition comprising (i) a peptide having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences ID nos. 1 to 10, and a derivative or salt thereof, and (ii) at least one pharmaceutically or cosmetically acceptable ingredient.

More in particular, the skin conditions mediated by the muscarinic receptor M3 activity which can be ameliorated by the non-therapeutic method of the present invention relates to excessive perspiration, sebum production, local inflammation, and/or cell adhesion, motility, growth, differentiation and proliferation.

A further aspect of the present invention relates to a polynucleotide that codes a peptide having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences ID nos. 1 to 10.

DETAILED DESCRIPTION OF THE INVENTION

According to a first aspect, the present invention relates to peptides having length equal to or lower than 20 amino acids, preferably equal to or lower than 15 amino acids, and comprising any one of the sequences ID nos. 1 to 10, or a sequence having at least 70%, preferably at least 80%, and more preferably at least 90% sequence identity with any one of the sequences nos. ID 1 to 10, and a derivative or salt thereof.

Preferably, the present invention relates to peptides having length equal to or lower than 15 amino acids, more preferably equal to or lower than 10, most preferably equal to or lower than 6, and comprising any one of the sequences ID nos. 1 to 5, or a sequence having at least 70%, preferably at least 80%, and more preferably at least 90% sequence identity with any one of the sequences nos. ID 1 to 5, and a derivative or salt thereof.

More preferably, the present invention relates to peptides other than peptide ALWMRL, said peptides having length equal to or lower than 15 amino acids, preferably equal to or lower than 10, and comprising any one of the sequences ID nos. 1 to 5, or a sequence having at least 70%, preferably at least 80%, and more preferably at least 90% sequence identity with any one of the sequences nos. ID 1 to 5, and a derivative or salt thereof.

Advantageously, the present invention relates to a peptide other than peptide ALWMRL, said peptide having length equal to or lower than 15 amino acids, preferably equal to or lower than 10, and comprising the sequence ID no. 1, or a sequence having at least 70%, preferably at least 80%, and more preferably at least 90% sequence identity with the sequence no. ID 1, and a derivative or salt thereof.

In a further aspect, the present invention relates to a peptide having length equal to or lower than 15 amino acids, preferably equal to or lower than 10, and starting with the sequence ID no. 1, or with a sequence having at least 70%, preferably at least 80%, and more preferably at least 90% sequence identity with the sequence no. ID 1, and a derivative or salt thereof.

In another aspect, the present invention relates to a peptide having length equal to or lower than 15 amino acids, preferably equal to or lower than 10, and comprising the sequence ID no. 2, or a sequence having at least 70%, preferably at least 80%, and more preferably at least 90% sequence identity with the sequence no. ID 2, and a derivative or salt thereof.

In a further aspect, the present invention relates to a peptide having length equal to or lower than 15 amino acids, preferably equal to or lower than 10, and comprising the sequence ID no. 3, or a sequence having at least 70%, preferably at least 80%, and more preferably at least 90% sequence identity with the sequence no. ID 3, and a derivative or salt thereof.

In another aspect, the present invention relates to a peptide having length equal to or lower than 15 amino acids, preferably equal to or lower than 10, and comprising the sequence ID no. 4, or a sequence having at least 70%, preferably at least 80%, and more preferably at least 90% sequence identity with the sequence no. ID 4, and a derivative or salt thereof.

In another aspect, the present invention relates to a peptide having length equal to or lower than 15 amino acids, more preferably equal to or lower than 10, and comprising the sequence ID no. 5, or a sequence having at least 70%, preferably at least 80%, and more preferably at least 90% sequence identity with the sequence no. ID 5, and a derivative or salt thereof.

Preferably, the present invention relates to peptides having length equal to or lower than 20 amino acids, preferably equal to or lower than 15 amino acids, and comprising any one of the sequences ID nos. 6 to 10, or a sequence having at least 70%, preferably at least 80%, and more preferably at least 90% sequence identity with any one of the sequences nos. ID 6 to 10, and a derivative or salt thereof.

According to a preferred aspect, the present invention relates to a peptide having length equal to or lower than 20 amino acids, preferably equal to or lower than 15 amino acids, and comprising the sequence ID no. 6, or a sequence having at least 70%, preferably at least 80%, and more preferably at least 90% sequence identity with the sequence no. ID 6, and a derivative or salt thereof.

According to a preferred aspect, the present invention relates to a peptide having length equal to or lower than 20 amino acids, preferably equal to or lower than 15 amino acids, and comprising the sequence ID no. 7, or a sequence having at least 70%, preferably at least 80%, and more preferably at least 90% sequence identity with the sequence no. ID 7, and a derivative or salt thereof.

According to a preferred aspect, the present invention relates to a peptide having length equal to or lower than 20 amino acids, preferably equal to or lower than 15 amino acids, and comprising the sequence ID no. 8, or a sequence having at least 70%, preferably at least 80%, and more preferably at least 90% sequence identity with the sequence no. ID 8, and a derivative or salt thereof.

According to a preferred aspect, the present invention relates to a peptide having length equal to or lower than 20 amino acids, preferably equal to or lower than 15 amino acids, and comprising the sequence ID no. 9, or a sequence having at least 70%, preferably at least 80%, and more preferably at least 90% sequence identity with the sequence no. ID 9, and a derivative or salt thereof.

According to a preferred aspect, the present invention relates to a peptide having length equal to or lower than 20 amino acids, preferably equal to or lower than 15 amino acids, and comprising the sequence ID no. 10, or a sequence having at least 70%, preferably at least 80%, and more preferably at least 90% sequence identity with the sequence no. ID 10, and a derivative or salt thereof.

To the best knowledge of the named inventors and applicant of the present application, none of the peptides described herein is known in the art before the priority date of the present application, other than peptide ALWMRL. However, any peptide known in the art before the priority date of the present application falling within the scope of the present invention is herein properly disclaimed.

Abbreviations of the amino acid sequences used herein are in accordance with the IUPAC-IUB nomenclature as reported in the following Table A.

TABLE A

| Alanine | Ala | A | Arginine | Arg | R |
| --- | --- | --- | --- | --- | --- |
| Asparagine | Asn | N | Aspartic acid | Asp | D |
| Cysteine | Cys | C | Glutamic acid | Glu | E |
| Glutamine | Gln | Q | Glycine | Gly | G |
| Histidine | His | H | Isoleucine | Ile | I |
| Leucine | Leu | L | Lysine | Lys | K |
| Methionine | Met | M | Phenylalanine | Phe | F |
| Proline | Pro | P | Serine | Ser | S |
| Threonine | Thr | T | Tryptophan | Trp | W |
| Tyrosine | Tyr | Y | Valine | Val | V |

"Percentage sequence identity" with respect to a peptide sequence refers to the percentage of residues that are identical in two sequences. The percent sequence identity (% SI) is calculated by the following formula:

% SI=(nt−nd)×100/nt wherein nt is the number of residues in the basic sequence and nd is the total number of non-identical residues in the confronted sequence when aligned so that a maximum number of amino acids are identical. Accordingly, a sequence WMNLK$\underline{S}$ will have a sequence identity of 83.3% with the sequence ID. No 4 WMNLK$\underline{T}$ (nd=1 and nt=6).

Peptide according to the invention may have at least 70%, at least 75%, at least 80%, at least 85%, at least 90% and at least 95% sequence identity to a reference sequence when optimally aligned. Optimal alignment of the sequences may be conducted by various known methods and computerized implementation of known algorithms (e.g. BLAST, TFASTA, BESTFIT, such as in the Wisconsin Genetics Software Package, Release 7.0, Genetics Computer Group, Madison, Wis.). The BLAST algorithm (Altschul et al., (1990), Mol. Biol. 215:403-10) for which software may be obtained through the National Center for Biotechnology Information (www.ncbi.nlm.nih.gov/) may also be used.

Variation of the amino acid sequence in the peptides comprising the sequences ID nos. 1 to 10 of the present invention comprises conservative substitution of amino acids that do not influence peptide activity. The substitutions able to maintain the peptide activity are selected on the basis of (a) the efficacy in maintaining the structure of the peptide backbone in the area of substitution, such as sheet or helical three-dimensional structures, (b) the efficacy in maintaining electrical charge or hydrophobicity of the molecule in the target area, or (c) the efficacy of maintaining the bulk of the side chain.

Amino acids are classified according to general side chain properties as described in the following Table B.

TABLE B

| hydrophobicity | NorLeucine, Met, Ala, Val, Leu, Ile; |
| --- | --- |
| neutral hydrophobicity | Cys, Ser, Thr; |
| acidity | Asp, Glu; |
| basicity | Asn, Gln, His, Lys, Arg; |
| residue that affects chain orientation | Gly, Pro; |
| aromaticity | Trp, Tyr, Phe. |

Examples of conservative substitution belong to the group consisting of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine, and threonine).

The amino add substitutions that do not generally alter the specific activity are known in the art of the present invention.

Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Another example of conservative substitutions are shown in the following Table C.

TABLE C

| Starting amino acid | Possible substitution | Preferred substitution |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norLeucine | Leu |
| Leu (L) | norLeucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |

TABLE C-continued

| Starting amino acid | Possible substitution | Preferred substitution |
| --- | --- | --- |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norLeucine | Leu |

The peptide of the present invention may be in the form of a modified peptide, of which N- or/and C-terminal is chemically modified or protected with organic compounds.

The term "derivative" or "derivative thereof" as employed herein in relation to a peptide of the present invention means a peptide wherein the N- and/or C-terminal thereof is chemically modified or protected with an organic compound.

Examples of modification include phosphorylation, glycosylation, acylation (including acetylation, lauroylation, myristorylation, palmitoylation), alkylation, carboxylation, hydroxylation, glycation, biotinylatlon, ubiquitinylation, and amidation.

Preferably, the peptide of the present invention may be modified at the N-terminal thereof, more preferably by acylation, including acetylation, lauroylation, myristorylation, and palmitoylation. N-terminal acetyl and palmitoyl peptide derivatives are a preferred aspect of the present invention.

The term "salt" or "salt thereof" as employed herein in relation to a peptide of the present invention means a salt of a peptide or derivative thereof with a suitable acid or base.

Typical examples of acids include, for example, hydrochloric acid, acetic acid, trifluoroacetic acid, oxalic acid, maleic acid, methanesulfonic acid, para-toluenesulfonic acid, succinic acid, citric acid, tartaric acid, and lactic acid.

Typical examples of bases include, for example, mono-, di- and trialkylamines, for instance methylamine, dimethylamine, trimethylamine, ethylamine, diethylamine, triethylamine, propylamine, dipropylamine, tripropylamine, ethylenediamine, mono-, di- and trialkanolamines, for instance monoethanolamine, diethanolamine and triethanolamine; guanidine, morpholine, piperidine, pyrrolidine, piperazine, 1-butylpiperidine, 1-ethyl-2-methyl-piperidine, N-methylpiperazine, 1,4-dimethylpiperazine, N-benzylphenylethylamine, N-methylglucosamine, and tris(hydroxymethyl)aminomethane.

An acetate or trifluoroacetate salt of a peptide, or a derivative thereof, is preferably employed under the present invention.

Depending on its length, the peptide of the present invention may be synthesized by a method well known in the art, for example, by an automated peptide synthesizer, or produced by a genetic engineering technology. For example, a fusion gene encoding a fusion protein including a fusion partner and the peptide of the present invention is prepared by genetic engineering, and then transformed into a host cell to express the fusion protein. Thereafter, the peptide of the present invention is cleaved and isolated from the fusion protein using a protease or a compound so as to produce the desired peptide. To this end, a DNA sequence encoding amino acid residues which can be cleaved by a protease such as Factor Xa or enterokinase, or a compound such as CNBr or hydroxylamine may be inserted between the polynucleotides encoding the fusion partner and the peptide of the present invention.

The peptides of the present invention may exist as stereoisomers or mixtures of stereoisomers; for example, the amino acids that make them up can have L-configuration, D-configuration or be racemic independently from each other. Therefore, it is possible to obtain isomeric mixtures as well as racemates or diastereomeric mixtures or pure diastereomers or enantiomers, depending on the number of asymmetric carbons and what isomers or isomeric mixtures are present. The preferred structures of the peptides of the present invention are pure isomers, i.e., enantiomers or diastereomers. The most preferred structures of the peptides of the present invention include amino acids having the L-configuration. Unless otherwise indicated, it is understood that when it is indicated that one amino acid can be Ala, it is understood that it is selected from L-Ala-, D-Ala- or racemic or non-racemic mixtures of both.

The cosmetic composition of the present invention comprises at least one of the above described peptides together with at least one cosmetically acceptable ingredient.

The pharmaceutical composition of the present invention comprises at least one of the above described peptides together with at least one pharmaceutically acceptable ingredient.

The pharmaceutical or cosmetic composition of the present invention can comprise an amount of the peptide, or a derivative and/or salt thereof, ranging from 0.00000001% to 20% by weight, preferably from 0.000001% to 15% by weight, more preferably from 0.0001% to 10% by weight, and even more preferably from 0.0001% to 5% by weight.

The cosmetic composition of the present invention can contain a variety of other optional components suitable for rendering such compositions more cosmetically or aesthetically acceptable or to provide them with addition usage benefits. Such conventional optional ingredients are well-known to those skilled in the art. These include any cosmetically acceptable ingredients such as those found in the CTFA International Cosmetic Ingredient Dictionary and Handbook, 7th edition, edited by Wenninger and McEwen, (The Cosmetic, Toiletry, and Fragrance Association, Inc., Washington, D.C., 1997). As used herein "cosmetically acceptable" means a material (e. g., compound or composition) which is suitable for use in contact with skin, hair or other suitable substrate as defined hereinbelow.

Cosmetically acceptable ingredients useful in the present invention includes cosmetically acceptable carriers, volatile and non-volatile solvents, water, and other additional ingredients, such as surfactants, preservatives, absorbents, chelating agents, lubricants, moisturizers water repellents, antioxidants, UV absorbers, anti-irritants, vitamins, trace metals, anti-microbial agents, perfumes, dyes and colour ingredients, and/or structuring agents.

The expression "cosmetically acceptable carrier", as used herein, means one or more compatible solid or liquid fillers, diluents, extenders and the like, which are cosmetically acceptable as defined hereinabove. The term "compatible", as used herein, means that the components of the compositions of this invention are capable of being combined with the primary actives of the present invention, and with each other, in a manner such that there is no interaction which would substantially reduce the efficacy of the composition under ordinary use situations.

The type of carrier utilized in the present invention depends on the type of product desired. The compositions useful in the present invention may be a wide variety of product forms. These include, but are not limited to, lotions, creams, gels, sticks, sprays, ointments, pastes, mousses and cosmetics (e. g., solid, semi-solid, or liquid make-up, including foundations).

These product forms may comprise several types of carriers including, but not limited to, solutions, aerosols, emulsions (including oil-in-water or water-in-oil), gels, solids, and liposomes.

The compositions of the present invention may comprise water, in different amounts depending on the form of the composition. The amount of water, if present, can range from less than 1% to more than 99% by weight with respect to the weight of total composition. The aqueous composition of the present invention are especially formulated as aqueous lotions or as water-in-oil or oil-in-water emulsions or as multiple emulsions (oil-in-water-in-oil or water-in-oil-in-water triple emulsion). Such emulsions are known and described, for example, by C. FOX in "Cosmetics and Toiletries"—November 1986—Vol. 101—pages 101-112.

Solid compositions, spray compositions, and water-in-oil creams usually comprise amounts of water lower than 10%, more preferably lower than 5% by weight with respect to the total weight of the composition. Roll-on compositions, aqueous compositions, and deodorant usually comprises amount of water from about 15% to about 99%, more preferably from about 30% to about 90%, even more preferably about 50% to about 80%, by weight with respect to the total weight of the composition.

The compositions of the present invention may also comprise silicones. If present, the silicones will generally be at a level of from about 30% to about 85%, more preferably from about 40% to about 75%, even more preferably about 50% to about 65%, by weight with respect to the total weight of the composition.

The silicones useful herein are preferably linear or cyclic silicones having from 2 to 7 silicone atoms, these silicones being optionally substituted with alkyl or alkoxy groups of 1 to 10 carbon atoms. Suitable silicones include dodecamethylcyclohexasiloxane, cyclopentasiloxane, decamethylcyclopenta siloxane, cyclotetrasiloxane, heptamethyloctyltrisiloxane, hexamethyldisiloxane, decamethyltetrasiloxane, dodeca-methylpentasiloxane octamethyltetrasiloxane and mixtures thereof.

The compositions of the present invention may comprise one or more volatile solvent. If present, the volatile solvent or mixture of solvents will generally be at a level of from about 10% to about 90%, more preferably from about 25% to about 75%, even more preferably about 35% to about 65%, by weight with respect to the total weight of the composition. The solvents useful herein are preferably organic volatile solvents.

As used herein, "volatile" refers to substances with a significant amount of vapour pressure under ambient conditions, as is understood by those in the art.

The volatile solvents for use herein will preferably have a vapour pressure of about 2 kPa or more, more preferably about 6 kPa or more, at 25° C. The volatile solvents for use herein will preferably have a boiling point under normal atmosphere (1 atm) of less than about 150° C., more preferably less than about 100° C., even more preferably less than about 90° C., even more preferably still less than about 80° C.

Preferably, the volatile solvents for use herein will be relatively odourless and safe for use on human skin. Suitable volatile solvents include, but are not limited to C1-C4 alcohols, volatile silicones and mixtures thereof. Preferred volatile solvents are C1-C4 alcohols and mixtures thereof. More preferred for use herein is ethanol.

The compositions of the present invention may also comprise one or more non-volatile solvent. If present, the non-volatile solvent or mixture of solvents will generally be at a level of from about 1% to about 20%, more preferably from about 2% to about 10%, even more preferably from about 3% to about 5%, by weight with respect to the total weight of the composition. Suitable non-volatile solvents include, but are not limited to, benzyl benzoate, cetearyl alcohol, cetyl alcohol, diethyl phthalate, isopropyl myristate, dimethicone, caprylylmethicone, and mixtures thereof.

Several other additional ingredients can be present in the compositions of the present invention. These include, but are not limited to, hydrophilic polymers selected from polyethylene glycols (PEGs), polyvinylpyrrolidones (PVP), hydroxypropyl methylcellulose (HPMC) and poloxamers; UV stabilizers such as benzophenone-3; antioxidants such as tocopheryl acetate; preservatives such as phenoxyethanol, benzyl alcohol, methyl paraben, propyl paraben; pH adjusting agents such as lactic acid, citric acid, sodium citrate, succinic acid, phosphoric acid, sodium hydroxide, sodium carbonate; deodorants and anti-microbials, such as farnesol, zinc phenolsulphonate, and ethylhexylglycerin; humectants such as tribehenin, glycerine; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; propellants such as propane, isopropane, butane, and isobutene; salts in general, such as potassium acetate and sodium chloride and mixtures thereof; perfumes and dyes.

If present, these additional ingredients will preferably be present at a level of less than 10%, more preferably of less than 5%, by weight with respect to the total weight of the composition.

Preferably, the pharmaceutical composition of the present invention is prepared in suitable dosage forms comprising an effective amount of at least one of the above described peptides together with at least one pharmaceutically acceptable ingredient.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions. Other suitable dosage forms are those with sustained release and those based on liposomes for oral, injectable or transdermal administration.

As described herein, the pharmaceutical composition of the present invention comprises at least one of the above described peptides together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

The dosage forms can also contain other traditional ingredients such as: preservatives, stabilizers, surfactants, buffers, salts for regulating osmotic pressure, emulsifiers, sweeteners, colorants, flavourings and the like.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions of this invention may also be administered by nasal aerosol or inhalation or delivered by implantation (e.g., surgically), such as with an implantable or indwelling device like a stent.

The dosage forms of the pharmaceutical composition of the present invention can be prepared by techniques that are familiar to a pharmaceutical chemist, and comprise mixing, granulation, compression, dissolution, sterilization and the like.

The peptides of the present invention are able to inhibit, or at least reduce, the interaction of acetylcholine with M3 receptor subtypes.

Accordingly, a further aspect of the present invention relate to the use of at least one of the above described peptides, and a derivative or salt thereof, for ameliorating skin conditions mediated by the muscarinic receptor M3 activity.

Further, the present invention also relates to a therapeutic or non-therapeutic method for ameliorating skin conditions mediated by the muscarinic receptor M3 activity comprising the topical application of a pharmaceutical or cosmetic composition comprising (i) at least one of the above described peptides, and a derivative or salt thereof, and (ii) at least one pharmaceutically or cosmetically acceptable ingredient.

In particular, the skin conditions mediated by the muscarinic receptor M3 activity include excessive perspiration, inflammation, sebum production, and cell adhesion, motility, growth, differentiation and proliferation.

More in particular, the skin conditions mediated by the muscarinic receptor M3 activity include (i) papulosquamous and eczematous dermatoses, such as atopic dermatitis, allergic contact dermatitis, irritant contact dermatitis, other eczematous disorders such as seborrhoeic dermatitis and other eczematous disorders, (ii) vesiculobullous diseases, such as Pemphigus, pemphigoid, dermatitis herpetiformis, epidermalysis bullosa, linear IgA dermatosis and other bullous disorders, (iii) adnexal diseases, such as acne vulgaris, acne rosacea (rosacea), perioral dermatitis, folliculitis, hyperhidrosis, Grover's disease, (iv) skin symptoms of rheumatologic disorders, such as dermatomyositis, systemic sclerosis, mixed connective tissue disease and cutaneous manifestations of rheumatologic disorders, (v) exposure to physical agents, such as radiation, including UV light and sunburn, heat, cold, frictional and traumatic injuries, normal or abnormal aging of the skin, including wrinkles, (vi) urticaria erythema and purpura, such as urticaria and angioedema, erythema multiforme, erythema annuare centrifugum and other erythmatous disorders, drug reactions of the skin, vasculitis and purpura of the skin, neutrophilic dermatoses and pregnancy dermatoses, and (vii) other skin disorders, such as pruritus, neuralgia, abnormal sensation or pain states, such as burning, or edema of the skin.

A further aspect of the present invention relates to a polynucleotide that codes at least one of the above described peptides.

The polynucleotide mentioned above enables production of the peptides of the present invention in large quantities. For example, cultivation of vectors that include polynucleotides encoding peptides allows production of peptides in large quantities.

A polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

The following examples are intended to better illustrate the present invention without however limiting it.

EXAMPLES

Example 1: Chemical Synthesis

All peptides were synthetized with the C terminus amidated using the standard Fmoc solid-phase method (Perez de la Vega et al., Molecules 2010, 15(7):4924-4933; Behrendt et al., J. Pept. Sci. 2016, 22(1):4-27; Made et al., Beilstein J. Org. Chem. 2014, 10:1197-1212). Synthesis of the peptides of invention, mixtures and/or their cosmetically or pharmaceutically acceptable salts can be carried out according to the conventional methods, known in the prior art, such as solid phase peptide synthesis methods, enzymatic synthesis or any combination (Bondazky et al., Int. J. Pept. Protein Res. 1993, 42(1):10-3).

All synthetic processes were carried out with Kromasil-C18-HPLC (5 µm, 4.6×250 mm). After, peptides were eluted with linear gradients of acetonitrile ($CH_3CN$) with Trifluoroacetic acid (TFA) (gradient: 5-55% B in 2 min, flow: 1 mL/min, eluent A: 100% $H_2O$+0.1% TFA; eluent B: 100% $CH_3CN$+0.1% TFA). Peptides detection was performed by measuring absorbance at 220 nm. The Fmoc group was removed with 20% piperidine/DMF solution for 30 min reaction. Washes between stages were carried out with DMF (5 times). All synthetic reactions and washes were performed at 25° C. HPLC analysis of the obtained peptides showed a purity exceeding 80% in all cases. The identity of the peptides obtained was confirmed by ESI-MS.

Process for introducing the Nt-acetyl group onto the peptidyl resins: 1 mmol (1 equivalent) of the peptidyl resins was treated with 25 equiv of pre-dissolved acetic anhydride in the presence of 25 equiv of DIEA, using 5 mL of DMF as solvent. After 30 min reaction, peptide resins were washed with DMF (1 min×5), DCM (1 min×4), and diethyl ether (1 min×4). Finally, peptidyl resins were dried under vacuum.

Process for introducing the Nt-palmitoyl group onto the peptidyl resins: 3 mmol (3 equiv) of pre-dissolved palmitic acid were incorporated onto peptidyl resins, in the presence of 3 equiv of HTBU and 6 equiv of NMM. They were allowed to react for 30-60 minutes using DMF as reagent.

Afterwards, resins were washed 3 times with DMF. Equivalent process for Nt-mysristoyl peptides.

Cleavage process from the polymeric support of the peptidyl resins: Dried peptidyl resins were treated with TFA:TIS:$H_2O$ (95:2.5:2.5) for 2 hours at 25° C. under vibration.

Example 2: Inhibition of M3-Acetylcholine Activation by the Peptides of the Invention Epithelial stable cell line constitutively expressing human muscarinic receptor M3 was used to assess peptides activity. Cells were seeded in 96-well plates at 50% cell confluence in 100 μL of complete Ham's F-12 medium. After 24 hours, medium was removed and cells were incubated with 90 μL/well of a solution of the peptides of the invention at 100, 50 or 10 μM or DMSO as vehicle. Peptides were dissolved in Fluo-4 NW (Invitrogen) fluorescent calcium probe assay buffer containing Probenecid, following manufacturer's instructions for 50 min at 37° C. in a $CO_2$ incubator. Afterwards, M3 activity was determined by reading the fluorescence in a FLUOstar Galaxy reader (BMG LabTechnologies) using 485 nm filter for excitation and 520 nm for emission, recording signal before and after M3 activation with 10 nM acetylcholine. Fluorescence measurements were normalized to acetylcholine maximum fluorescence signal in vehicle treated cells. Atropine (100 nM) was used as positive control for inhibition. Inhibition values of M3 activity were calculated as percentages by considering maximum fluorescence corresponding to acetylcholine-M3 activation and minimum as non-stimulated cells. Table D details inhibition values of M3 activity inhibition obtained for the peptides of invention.

The peptides were capable of inhibiting acetylcholine-evoked M3 activity in a range of 13-74% at 50 μM and 60-95% at 100 μM. Peptides seq. ID No. 2, 3 and 8 at 10 μM significantly inhibited M3 activity in a range of 40-60%.

Example 3: Time-Dependent Inhibition of M3 Activity

Peptides of invention were designed to target the intracellular region of M3. Therefore, minimum time required to detect inhibitory effect on M3 activity was evaluated. For this purpose, inhibitory effect of peptides Seq. ID No. 1-8 were characterized along time as those showed the strongest inhibition effect. Epithelial stable cell line constitutively expressing human muscarinic receptor M3 was used to assess peptides activity. Cells were seeded in 96-well plates at 50% cell confluence in 100 μL of complete Ham's F-12 medium. After 24 hours, medium was removed and cells were incubated with 90 μL/well of Fluo-4 NW (Invitrogen) fluorescent calcium probe assay buffer containing probenecid, following manufacturer's instructions at 37° C. in a $CO_2$ incubator. Peptides (50 μM), vehicle and atropine were incubated either with the probe (1 hour pre-incubation) or during fluorescence reading (direct effect). Afterwards, M3 activity was recorded for 20 cycles and direct effect peptides were added on cycle 3 after baseline assessment. Acetylcholine was added on cycle 13. Therefore, direct effect of peptides was monitored for 25 minutes. Inhibition values of M3 activity were calculated as percentages by considering maximum fluorescence corresponding to vehicle or non-treated cells acetylcholine-M3 activation and minimum as non-stimulated cells. Table E details inhibition values of M3 activity inhibition obtained for the peptides of invention.

TABLE D

| Peptide | Sequence | Nt-Derivatization | % M3 inhibition | | |
|---|---|---|---|---|---|
| | | | 100 μM | 50 μM | 10 μM |
| Seq. ID No. 1 | WMRL | Palmitoyl | 95.6 | 70.9 | 15.4 |
| Seq. ID No. 2 | WMRLK | Acetyl | 24.6 | 9.1 | 0.0 |
| | | Palmitoyl | 88.6 | 85.4 | 62.5 |
| Seq. ID No. 3 | WMRLKA | Palmitoyl | 75.7 | 73.7 | 41.0 |
| Seq. ID No. 4 | WMNLKT | Palmitoyl | 60.6 | 59.6 | 35.3 |
| Seq. ID No. 5 | WMFLK | Palmitoyl | 80.6 | 45.7 | 0.0 |
| | | Acetyl | 15.1 | 6.2 | 3.9 |
| Seq. ID No. 6 | RMYKMMAGMYLR | Myristoyl | 92.1 | 56.4 | 14.8 |
| | | Palmitoyl | — | — | 34.5 |
| | | Acetyl | 32.5 | 26.4 | 3.0 |
| Seq. ID No. 7 | RVMYKMNKRDY | Myristoyl | 92.4 | 54.8 | 15.9 |
| | | Palmitoyl | — | — | 47.4 |
| | | Acetyl | 20.6 | 8.3 | 8.6 |
| Seq. ID No. 8 | RVMFKMFKRDY | Myristoyl | 93.8 | 71.7 | 42.5 |
| | | Palmitoyl | — | — | 32.7 |
| | | Acetyl | 26.1 | 12.4 | 21.5 |
| Seq. ID No. 9 | RMTMLMLDFKYMKWW | Acetyl | 23.3 | 6.3 | 1.2 |
| Seq. ID No. 10 | KMTMRMLYFKYMMWW | Myristoyl | 65.0 | 19.0 | 5.2 |
| | | Palmitoyl | — | 53.4 | 39.3 |
| | | Acetyl | 65.0 | 19.0 | 5.2 |

TABLE E

| Peptide | Sequence | Nt-Derivatization | % Inhibition hM3 receptor activity | |
|---|---|---|---|---|
| | | | 25 minutes | 60 minutes |
| Seq. ID No. 1 | WMRL | Palmitoyl | 25.1 | 69.5 |
| Seq. ID No. 2 | WMRLK | Palmitoyl | 25.5 | 81.0 |
| Seq. ID No. 3 | WMRLKA | Palmitoyl | 16.4 | 73.0 |
| Seq. ID No. 4 | WMNLKT | Palmitoyl | 11.5 | 69.1 |
| Seq. ID No. 5 | WMFLK | Palmitoyl | -7.1 | 84.4 |
| Seq. ID No. 6 | RMYKMMAGMYLR | Myristoyl | -20.2 | 54.7 |
| Seq. ID No. 7 | RVMYKMNKRDY | Myristoyl | 16.4 | 82.7 |
| Seq. ID No. 8 | RVMFKMFKRDY | Myristoyl | 6.1 | 87.1 |

Quantification of M3 response showed that peptides Seq. ID No. 1-8 were effective at 50 μM after 1 hour pre-incubation.

Example 4: Dose-Response Inhibitory Effect

Characterization of Seq. ID No. 1, 3-8 peptides efficiency was obtained by calculating half maximal inhibitory concentration ($IC_{50}$). For this purpose, experimental procedure regarding cell culture and fluorescent calcium probe assay was followed as described on Example 2. Peptides were assessed at concentrations between 0.1 and 100 μM and incubated for 1 hour together with Fluo-4 NW probe. Afterwards, M3 activity was determined by reading the fluorescence in a FLUOstar Galaxy reader (BMG LabTechnologies) using 485 nm filter for excitation and 520 nm for emission, recording signal before and after M3 activation with acetylcholine. Fluorescence measurements were standardized with regard to the maximum fluorescence signal detected with acetylcholine stimulation in vehicle treated cells. Inhibition values of M3 activity were calculated as percentages by considering maximum fluorescence corresponding to acetylcholine-M3 activation and minimum as non-stimulated cells. Percentage inhibition data was fitted to a sigmoidal curve to obtain $IC_{50}$. Table F details inhibition values for $IC_{50}$

TABLE F

| Peptide | Sequence | Nt-Derivatization | IC50 [μM] |
|---|---|---|---|
| Seq. ID No. 1 | WMRL | Palmitoyl | 38.3 |
| Seq. ID No. 2 | WMRLK | Palmitoyl | 7.2 |
| Seq. ID No. 3 | WMRLKA | Palmitoyl | 12.7 |
| Seq. ID No. 4 | WMNLKT | Palmitoyl | 8.0 |
| Seq. ID No. 5 | WMFLK | Palmitoyl | 61.1 |
| Seq. ID No. 6 | RMYKMMAGMYLR | Myristoyl | 55.2 |
| Seq. ID No. 7 | RVMYKMNKRDY | Myristoyl | 55.0 |
| Seq. ID No. 8 | RVMFKMFKRDY | Myristoyl | 9.8 |

TABLE F-continued

All peptides were effective within the same range of concentrations showing 50% efficacy between around 10 and 60 μM. The most potent peptides according to $IC_{50}$ obtained were Seq. ID No. 2, 4, 8 and 3, followed by 1, 6, 7 and 5.

Example 5: Cell Viability Assay in Human Keratinocytes and Fibroblasts

This example evaluated the effects of the tested peptides on human epidermal keratinocytes and dermal fibroblasts cell viability. The 3-(4,5-dimethyl-2-thiazolyl)-2,5-diphenyl-2H-tetrazolium bromide (MTT) assay was used to that monitor cell proliferation and viability based on the capacity of the mitochondrial dehydrogenase enzyme to break and transform the tetrazolium rings of MTT.

Epidermal keratinocytes were seeded in a previously coated 96 well-plate at 50-60% confluence in 100 μL of supplemented medium. Dermal fibroblasts were seeded in a 96 well-plate at 70% confluence in 100 μL supplemented medium. 24 hours after seeding, medium was replaced by fresh supplemented medium containing peptides dissolved at concentration range between 0.1 and 100 μM or SDS as reference of 100% toxicity or DMSO as vehicle for peptides. All test substances were incubated for 24 hours at 37° C. and 5% $CO_2$. Afterwards, medium was replaced by 0.5 mg/mL of MTT solution for 4 h in complete medium. Then, medium was carefully removed and 150 μL/well of DMSO were added to solubilize formazan crystals. Plate was protected from light, shaken for 60 seconds and optical density was measured at 570 nm with a reference filter of 620 nm. Toxicity values were calculated as percentages by considering maximum cytotoxic effect to SDS-treated cells and minimum as non-treated cells. Table G details effects of Seq. ID No 1, 5, 6 and 7 peptides on keratinocytes and fibroblasts as percentage of cell viability inhibition.

TABLE G

| Peptide | Sequence | Nt-Derivatization | µM | % Cell viability inhibition | |
|---|---|---|---|---|---|
| | | | | HEKa | HDFa |
| Seq. ID No. 1 | WMIRL | Palmitoyl (TFA salt) | 100 | 10.3 | -3.5 |
| | | | 50 | 8.9 | 0.1 |
| | | | 10 | -14.9 | 7.8 |
| | | Palmitoyl (Acetate salt) | 100 | 56.5 | 22.5 |
| | | | 50 | 39.7 | 8.2 |
| | | | 10 | 7.1 | 10.1 |
| | | | 5 | 3.8 | 9.2 |
| | | | 1 | -4.8 | 6.6 |
| | | | 0.1 | -9.5 | 5.2 |
| Seq. ID No. 5 | WMFLK | Palmitoyl (TFA salt) | 100 | 22.7 | 25.5 |
| | | | 50 | 14.5 | 22.7 |
| | | | 10 | -9.4 | 22.2 |
| | | Palmitoyl (Acetate salt) | 100 | 56.8 | 35.2 |
| | | | 50 | 49.6 | 31.9 |
| | | | 10 | 11.0 | 31.5 |
| | | | 5 | -9.1 | 27.2 |
| | | | 1 | -10.9 | 10.0 |
| | | | 0.1 | -18.7 | 3.6 |
| Seq. ID No. 6 | RMYKMMAGMYLR | Acetyl (TFA salt) | 100 | 17.1 | -9.9 |
| | | | 50 | 14.3 | -3.3 |
| | | | 10 | -13.0 | 4.0 |
| | | Myristoyl (TFA salt) | 100 | — | 29.3 |
| | | | 50 | — | 38.4 |
| | | | 10 | — | 43.7 |
| | | Myristoyl (Acetate salt) | 100 | 93.9 | 60.3 |
| | | | 50 | 80.0 | 35.2 |
| | | | 10 | 8.0 | 13.8 |
| | | | 5 | -12.2 | 10.6 |
| | | | 1 | -0.7 | 6.3 |
| | | | 0.1 | -4.3 | 1.3 |
| Seq. ID No. 7 | RVMYKMNKRDY | Acetyl (TFA salt) | 100 | 15.4 | 19.4 |
| | | | 50 | 20.7 | 11.5 |
| | | | 10 | -11.0 | 8.5 |
| | | Myristoyl (TFA salt) | 100 | — | 12.1 |
| | | | 50 | — | 8.7 |
| | | | 10 | — | 11.5 |
| | | Myristoyl (Acetate salt) | 100 | 96.4 | 48.5 |
| | | | 50 | 87.5 | 34.6 |
| | | | 10 | 1.53 | 14.0 |
| | | | 5 | 2.87 | 7.9 |
| | | | 1 | 1.43 | 1.7 |
| | | | 0.1 | 5.3 | 4.1 |

Peptides Seq. ID No 1, 5, 6 and 7 were assessed as TFA and/or acetate salt. In general, peptides as acetate-salt did not impair cell viability when tested at concentrations below 50 µM. On the contrary, Nt-palmitoyl-seq. ID No 1, Nt-palmitoyl-seq. ID No 5, Nt-acetyl-seq. ID No 6 and Nt-acetyl-seq. ID No 7 did not affect cell proliferation as TFA-salt at any concentration assessed.

Example 6: Evaluation the Antiperspirant Effect on Acute Administration in a Mouse Model of Sweat Secretion This example evaluated acute effects of the peptide of invention Seq. ID No 2, pamitoylated form, in an in vivo sweating model induced by pilocarpine. This model was established using pilocarpine, a non-selective agonist of muscarinic receptors, in 11-weeks old C57BL6/Rcc male mice.

Test compound is the peptide of the invention having the following sequence (Sequence ID No. 2):

Palm-WMMRLK-NH$_2$

Test compound was injected i.pl. on the right hind paw (10, 30 and 100 µg) 30 min before sweating stimulation. Vehicle was saline solution.

Sweating was monitored through amylase activity detection on skin surface using iodine/starch reaction. Dark sweating drops were quantified after 5 minutes induction counting number of drops per paw in each condition. Data are expressed as mean±standard error of the mean (SEM). Raw data was normalized as percentage respect to non-injected stimulated individuals (Control, 100%) and saline-injected non-stimulated individuals (Vehicle, 0%). Statistical analysis was one-way ANOVA followed by Dunnett's post-hoc multiple comparison test comparing each condition with the corresponding control group, **$p<0.0001$ *$p<0.001$ **$p<0.01$, *$p<0.05$ The results are summarized in the following Table G.

TABLE G

| Palm-Seq ID No. 2 | % Inhibition | SEM | Statistic |
|---|---|---|---|
| 10 µg/paw | 67.3 | ±5.4 | **** |
| 30 µg/paw | 63.2 | ±5.9 | **** |
| 100 µg/paw | 67.9 | ±7.5 | **** |

Test compound significantly reduced sweating at 10, 30 and 100 µg.

Example 7: Evaluation the Antiperspirant Effect on Chronic Administration in a Mouse Model of Sweat Secretion This example evaluated chronic effects of peptide of invention Seq. ID No. 2, palmitoylated form, in an in vivo sweating model. This model was established using pilocarpine, a non-selective agonist of muscarinic receptors, in 11-weeks old C57BL6/Rcc male mice. Test compound was locally administered three times per week for 4 weeks (Treatment). Sweat was induced by intraplantar (i.pl) injection of pilocarpine (3 μg/paw) in the right hind paw (Sweating) on weeks 1, 2 and 4 according to the table H.

TABLE H

| Week | Monday | Tuesday | Wednesday | Thursday | Friday |
|------|-----------|----------|-----------|----------|-----------|
| 1 | Treatment | Sweating | Treatment | — | Treatment |
| 2 | Treatment | Sweating | Treatment | — | Treatment |
| 3 | Treatment | — | Treatment | — | Treatment |
| 4 | Treatment | Sweating | Treatment | — | Treatment |

Test compound is the peptide of the invention having the following sequence (Sequence ID No. 2):

Palm-WMRLK-NH$_2$

Test compound was injected i.pl. on the right hind paw (1, 10 and 100 μg in). Vehicle injected was saline solution.

Sweating was monitored through amylase activity detection on skin surface using iodine/starch reaction. Dark sweating drops were quantified after 5 minutes induction counting number of drops per paw in each condition. Sample n=5-6 individuals per group. Data are expressed as mean±standard error of the mean (SEM). Raw data was normalized as percentage respect to non-injected stimulated individuals (Control, 100%). Statistical analysis was one-way ANOVA followed by Dunnett's post-hoc multiple comparison test comparing each condition with the corresponding control group, **$p<0.0001$ *$p<0.001$ **$p<0.01$, *$p<0.05$ The results are summarized in the following Table I.

TABLE I

| | Palm-Seq ID No2 | % Inhibition | SEM | Statistic |
|--------|-----------|------|-------|------|
| Week 1 | 1 μg/paw | 9.1 | ±11.1 | |
| | 10 μg/paw | 27.5 | ±4.5 | *** |
| | 100 μg/paw | 28.0 | ±4.7 | ** |
| Week 2 | 1 μg/paw | 22.2 | ±8.4 | * |
| | 10 μg/paw | 35.4 | ±4.5 | **** |
| | 100 μg/paw | 26.3 | ±4.8 | ** |
| Week 4 | 1 μg/paw | 10.7 | ±6.8 | |
| | 10 μg/paw | 27.9 | ±5.9 | **** |
| | 100 μg/paw | 29.7 | ±2.2 | **** |

Palm-Seq ID No 2 showed significant sweating inhibition during 4 weeks treatment when tested at 10 and 100 μg/paw.

---

The invention claimed is:

1. A peptide or a derivative or salt thereof having a length equal to or lower than 6 amino acids and that is different from peptide ALWMRL, wherein:
   said peptide or a derivative or salt thereof contains any one of sequences ID nos. 1 to 5, or
   said peptide or a derivative or salt thereof contains a sequence having at least 70% sequence identity with any one of the sequences nos. ID 1 to 5, and
   wherein in said derivative, an N-and/or C- terminal is chemically modified or protected with an organic compound.

2. The peptide or a derivative or salt thereof according to claim 1, which contains a sequence having at least 80% sequence identity with any one of the sequences nos. ID 1 to 5.

3. The peptide or a derivative or salt thereof according to claim 1, which contains a sequence having at least 90% sequence identity with any one of the sequences nos. ID 1 to 5.

4. The peptide or a derivative or salt thereof according to claim 1, wherein said organic compound is selected from the group consisting of a phosphoryl, glycosyl, acyl, alkyl, carboxyl, hydroxyl, biotinyl, ubiquitinyl, and amido group.

5. The peptide or a derivative or salt thereof according to claim 4, wherein said acyl group is selected from the group consisting of an acetyl, lauroyl, myristoryl, and palmitoyl group.

6. The peptide or a derivative or salt thereof according to claim 1, wherein said N-terminal thereof is chemically modified or protected with an acetyl or a palmitoyl group.

7. The peptide or a derivative or salt thereof according to claim 1, wherein said salt is a salt of said peptide or derivative thereof with a suitable acid or base.

8. The peptide or a derivative or salt thereof according to claim 7, wherein said acid is selected from the group consisting of hydrochloric acid, acetic acid, trifluoroacetic acid, oxalic acid, maleic acid, methanesulfonic acid, para-toluenesulfonic acid, succinic acid, citric acid, tartaric acid, and lactic acid.

9. The peptide or a derivative or salt thereof according to claim 7, wherein said acid is selected from the group consisting of hydrochloric acid, acetic acid and trifluoroacetic acid.

10. The peptide or a derivative or salt thereof according to claim 7, wherein said base is selected from the group consisting of a mono-, di-and trialkylamine, a mono-, di-and trialkanolamine, guanidine, morpholine, piperidine, pyrrolidine, piperazine, 1-butylpiperidine, 1-ethyl-2-methyl-piperidine, N- methylpiperazine, 1,4-dimethylpiperazine, N-benzylphenylethylamine, N-methylglucosamine, and tris (hydroxymethyl)aminomethane.

11. The peptide or a derivative or salt thereof according to claim 1 wherein at least one amino acid as listed in the left column of the following table of any one of said sequences ID nos. 1 to 5 is substituted with an amino acid as listed in the right column of the following table, provided that the resulting sequence has at least 70% sequence identity with any one of said sequences nos. ID 1 to 5, respectively

| Starting amino acid | Substitution |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; norLeucine |
| Leu (L) | norLeucine; Ile; Val; Met; Ala; Phe |
| Lys (K) | Arg; Gln; Asn |
| Met (M) | Leu; Phe; Ile |
| Phe (F) | Leu; Val; Ile; Ala; Tyr |
| Pro (P) | Ala |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala; norLeucine. |

12. The peptide or a derivative or salt thereof according to claim 1 wherein at least one amino acid as listed in the left column of the following table of any one of said sequences ID nos. 1 to 5 is substituted with an amino acid as listed in the right column of the following table, provided that the resulting sequence has at least 70% sequence identity with any one of said sequences nos. ID 1 to 5, respectively

| Starting amino acid | Substitution |
| --- | --- |
| Ala (A) | Val |
| Arg (R) | Lys |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile |
| Lys (K) | Arg |
| Met (M) | Leu |
| Phe (F) | Tyr |
| Pro (P) | Ala |
| Ser (S) | Thr |
| Thr (T) | Ser |
| Trp (W) | Tyr |
| Tyr (Y) | Phe |
| Val (V) | Leu. |

13. A cosmetic composition, comprising (i) a peptide or a derivative or salt thereof as defined in claim 1, and (ii) at least one cosmetically acceptable ingredient.

14. A pharmaceutical composition comprising (i) a peptide or a derivative or salt thereof as defined in claim 1, and (ii) at least one pharmaceutically acceptable ingredient.

15. A therapeutic or non-therapeutic method for ameliorating a skin condition mediated by a muscarinic receptor M3 activity comprising applying topically to a subject in need thereof of a pharmaceutical or cosmetic composition comprising (i) a peptide or a derivative or salt thereof as defined in claim 1, and (ii) at least one pharmaceutically or cosmetically acceptable ingredient.

16. The method according to claim 15, wherein said skin condition mediated by the muscarinic receptor M3 activity is selected from the group consisting of excessive perspiration, inflammation, sebum production, and cell adhesion, motility, growth, differentiation and proliferation.

17. The peptide or a derivative or salt thereof according to claim 7, wherein said base is selected from the group consisting of methylamine, dimethylamine, trimethylamine, ethylamine, diethylamine, triethylamine, propylamine, dipropylamine, tripropylamine, ethylenediamine, monoethanolamine, diethanolamine, triethanolamine, guanidine, morpholine, piperidine, pyrrolidine, piperazine, 1-butylpiperidine, 1-ethyl-2-methyl-piperidine, N-methylpiperazine, 1,4-dimethylpiperazine, N-benzylphenylethylamine, N-methylglucosamine, and tris(hydroxymethyl)aminomethane.

18. A polynucleotide that codes a peptide or a derivative or salt thereof as defined in claim 1.

* * * * *